(12) United States Patent
Miyamoto et al.

(10) Patent No.: US 7,371,302 B2
(45) Date of Patent: May 13, 2008

(54) METHOD FOR FORMING FASTENING MEMBERS

(75) Inventors: Kouichi Miyamoto, Kobe Hyogo (JP); Akiko Tsubota, Fujisawa Kanagawa (JP); Kiyomi Shimamura, Osaka Osaka (JP)

(73) Assignee: The Procter & Gamble Company, Cincinnati, OH (US)

( * ) Notice: Subject to any disclaimer, the term of this patent is extended or adjusted under 35 U.S.C. 154(b) by 222 days.

(21) Appl. No.: 10/623,882

(22) Filed: Jul. 21, 2003

(65) Prior Publication Data

US 2004/0016499 A1   Jan. 29, 2004

Related U.S. Application Data

(60) Provisional application No. 60/398,043, filed on Jul. 23, 2002.

(51) Int. Cl.
*B32B 38/04*   (2006.01)
(52) U.S. Cl. .................. 156/269; 156/66; 156/264; 156/265; 83/46; 83/47
(58) Field of Classification Search ............... 156/250, 156/256, 66, 264, 265, 269; 83/46, 47, 56; 604/389, 391
See application file for complete search history.

(56) References Cited

U.S. PATENT DOCUMENTS

| 5,383,871 | A | | 1/1995 | Carlin et al. |
| 5,399,219 | A | | 3/1995 | Roessler et al. |
| 5,624,429 | A | * | 4/1997 | Long et al. ................. 604/391 |
| 5,759,317 | A | * | 6/1998 | Justmann .................... 156/66 |
| 5,851,205 | A | | 12/1998 | Hisada et al. |
| 5,876,531 | A | * | 3/1999 | Jacobs et al. ................ 156/66 |
| 6,030,373 | A | | 2/2000 | VanGompel et al. |
| 6,195,850 | B1 | * | 3/2001 | Melbye et al. ............... 24/304 |
| 6,230,374 | B1 | * | 5/2001 | Widlund .................... 24/586.1 |

FOREIGN PATENT DOCUMENTS

| EP | 0 755 665 A1 | 1/1997 |
| FR | 2810537 A1 | 6/2000 |

* cited by examiner

*Primary Examiner*—Mark A Osele
(74) *Attorney, Agent, or Firm*—Charles R. Matson; Thibault Fayette; Ken K. Patel (57) ABSTRACT

A method for forming a plurality of pairs of fastening members is disclosed. Each fastening member extends in a longitudinal direction and in a lateral direction and comprises a base panel and a tab extending laterally from the base panel. The tab has first fastening materials laterally spacedly positioned.

7 Claims, 9 Drawing Sheets

METHOD FOR FORMING FASTENING MEMBERS

CROSS REFERENCE TO RELATED APPLICATION

This application claims the benefit of U.S. Provisional Application No. 60/398,043, filed Jul. 23, 2002.

TECHNICAL FIELD

The present invention relates to a method for forming a plurality of pairs of fastening members, each fastening assembly comprising a base panel and a tab having fastening materials spacedly positioned.

BACKGROUND

Disposable absorbent articles are provided with a fastening means to form a closure of so-called open type absorbent articles when in use or to adjust the dimension of the waist circumference of so-called pull-on type absorbent articles. Such fastening means have been typically provided in the form of a fastening member comprising a substrate and a fastening material provided on the substrate. The fastening member has a manufacture end which is used to join the fastening member to the absorbent articles and a user end which is used for intended purpose of the fastening member. The fastening material comprising, e.g., at least one of the hook and loop component is positioned on the user end of the fastening member. In conventional fastening members, as only one piece of the fastening material is often provided on the user end of one fastening member, the fastening material on the user end sometimes disengages from the opposite fastening material provided on the other part of the absorbent article. Such disengagement of the fastening material on the user end is caused by the force exerted to the edge of the fastening material which is easily transmitted into the entire region of the fastening material.

U.S. Pat. No. 5,851,205 issued to Hisada et al. on Dec. 22, 1998 discloses a disposable undergarment having a tape fastener. The tape fastener includes a relatively soft base substrate extending laterally outwardly from a transverse side edge of the undergarment, relatively rigid fastening panel members provided at longitudinally spaced apart locations of the base substrate, and an adhesive region provided between the fastening panel members. It is stated that, even if one of the spaced apart fastening panel members, for example, the one provided in the proximity of the free end of the base substrate is unintentionally disengaged from the fastening region, the other one provided in the proximity of the base end of the base substrate will not be affected by the disengaging force exerted on the fastening panel member provided in the proximity of the free end of the base substrate. However, because the base substrate comprises one piece of the material, it is impossible to differentiate properties of the base substrate from a portion to a portion with respect to, e.g., stiffness and/or stretchability. Further, this publication does not disclose any method for effectively forming a plurality of pairs of fastening members, each fastening member comprising a panel and a tab having fastening materials spacedly positioned.

U.S. Pat. No. 6,030,373 issued to VanGompel et al. on Feb. 29, 2000 discloses multi-attachment fastening system. The user bond portion of the fastening tab includes a leading region and at least one trailing region thereof. The leading region is separated from the trailing region by a substantially non-securing spacing section. The securing means such as hook components are provided on the leading region and the trailing region. However, in this publication, the securing means is provided on the entirety of the leading region not to provide any spacing section at the leading edge of the leading region. Therefore, the leading edge of the leading region is securely attached to the means receiving the securing means. This inhibits the user from smoothly removing the securing means of the leading edge from the receiving member. Further, this publication does not disclose any method for effectively forming a plurality of pairs of fastening members, each fastening member comprising a panel and a tab having fastening materials spacedly positioned.

Based on the foregoing, there is a need for a method for effectively forming a plurality of pairs of fastening members, each fastening member comprising a base panel and a tab having fastening materials spacedly positioned. There is a also a need for a fastening material having a tab with regions of different properties. There is also a need for a fastening material having a tab with a grasp portion. None of the existing absorbent articles provides all of the advantages and benefits of the present invention.

SUMMARY

The present invention is directed to a method for forming a plurality of pairs of fastening members. Each fastening member extends in a longitudinal direction and in a lateral direction and comprises a base panel and a tab extending laterally from the base panel. The tab has first fastening materials laterally spacedly positioned. The method comprising the steps of: (a) preparing a continuous fastening composite web extending along a longitudinal direction; the continuous fastening composite web comprising two longitudinally extending first substrates laterally spacedly positioned, a longitudinally extending second substrate positioned between the two first substrates, and at least two longitudinally extending first fastening materials laterally spacedly positioned; each of the first substrate having a longitudinal outer side edge and a longitudinal inner side edge; the second substrate having a pair of longitudinal side edges; each of the first fastening material having a longitudinal inner side edge and a longitudinal outer side edge; wherein each of the longitudinal side edges of the second substrate is joined adjacent each of the longitudinal inner side edges of the first substrates, and each of the first fastening materials is joined on at least one of the first substrate and the second substrate to define a gap region between each of the longitudinal inner side edges of the first fastening materials and to define a pair of continuous panel regions between each of the longitudinal outer side edges of the first fastening materials and each of the longitudinal outer side edges of the first substrates; (b) cutting the continuous fastening composite web along a continuous cut line comprising a plurality of repeating patterns, each of the repeating patterns extending from one panel region through the two first fastening materials to reach the other panel region and extending to return from the other panel region through the two first fastening materials to reach the one panel region, thereby forming a pair of continuous fastening members, each continuous fastening member having a continuous panel region and a plurality of tabs, each tab having the two first fastening materials spacedly positioned; and (c) cutting each of the continuous fastening members across the continuous panel region, thereby forming a plurality of pairs of fastening members, each fastening member comprising the base panel and the tab.

All documents cited are, in relevant part, incorporated herein by reference; the citation of any document is not to be construed as an admission that it is prior art with respect to the present invention.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION

As used herein, the term "comprising" means that other steps and other ingredients which do not affect the end result can be added. This term encompasses the terms "consisting of" and "consisting essentially of."

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, and the like. The term "longitudinal", as used herein, refers to a line, axis or direction in the plane of the absorbent article that is generally aligned with (e.g., approximately parallel to) a vertical plane which bisects a standing wearer into left and right body halves when the absorbent article is worn. The terms "transverse" or "lateral" used herein, are interchangeable, and refer to a line, axis or direction which lies within the plane of the absorbent article that is generally perpendicular to the longitudinal direction.

Figure 1:
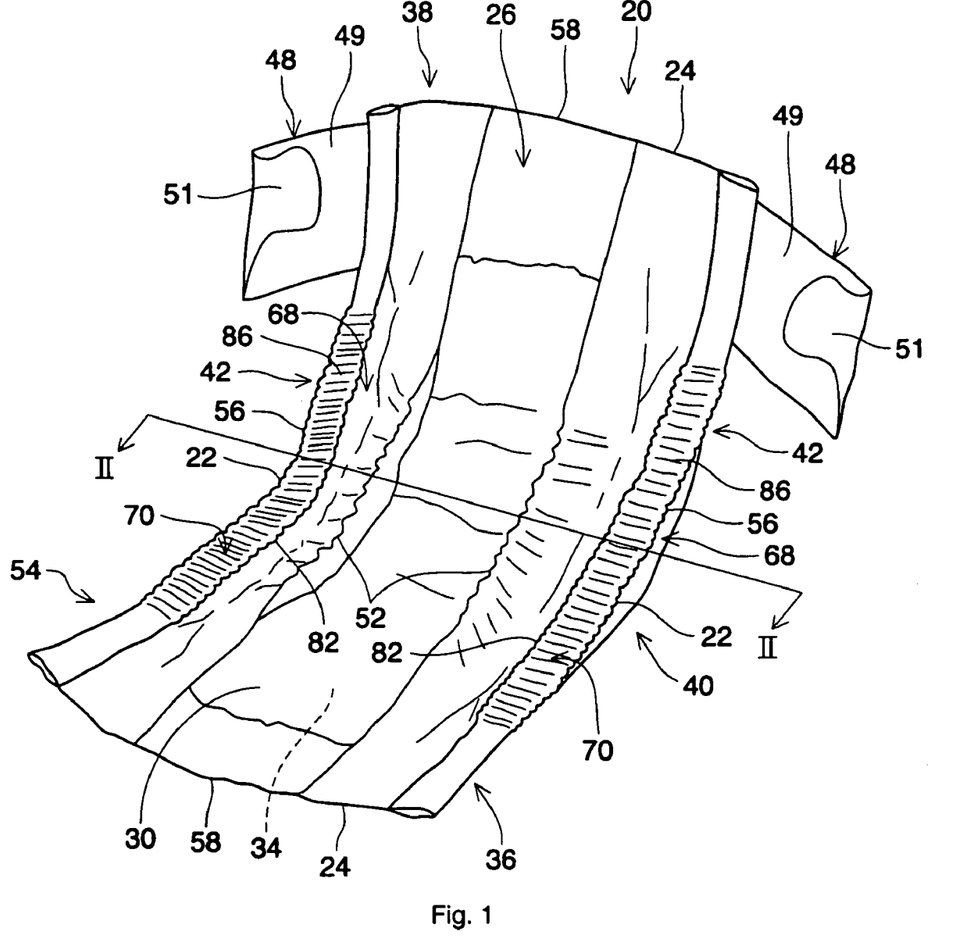
FIG. 1 is a perspective view of one embodiment of a diaper having a fastening member formed in accordance with the present invention.
Figure 2:
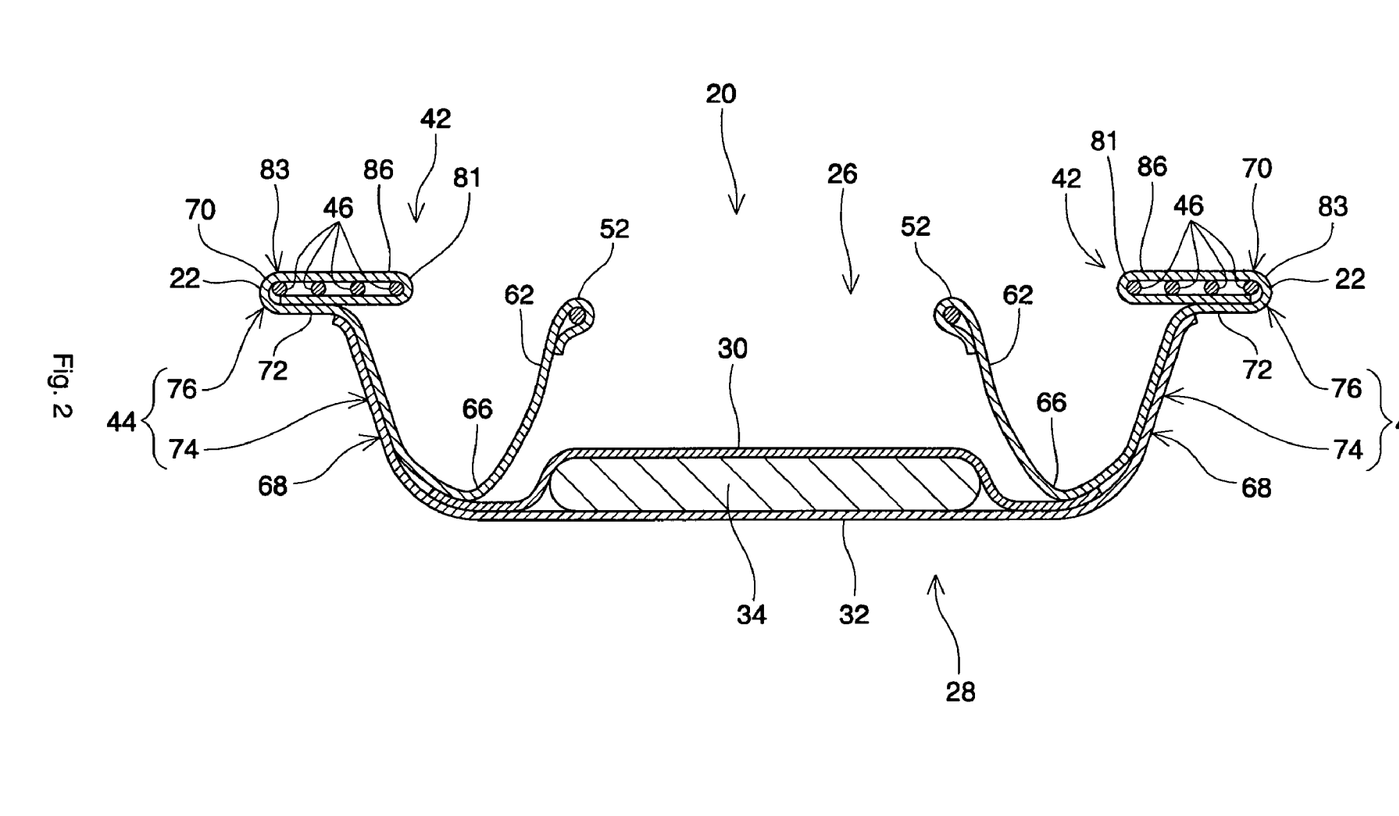
FIG. 2 is a cross-sectional view taken along the line II-II of FIG. 1.
Figure 3:
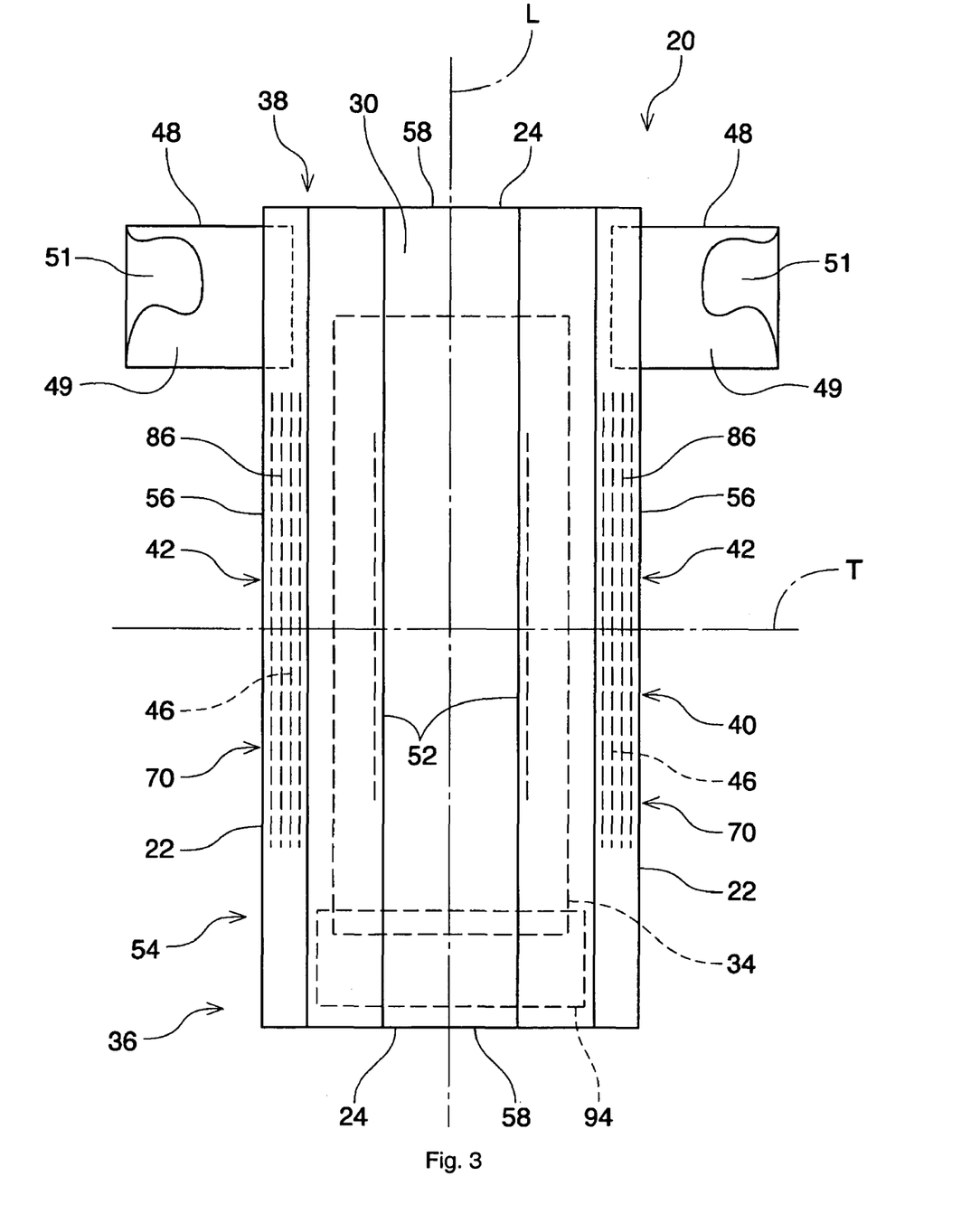
FIG. 3 is a top plan view of the diaper of FIG. 1 in its flat-out configuration.

FIG. 1 is a perspective view of the diaper 20 having a fastening member 48 of the present invention. Referring to FIG. 2 showing a cross-sectional view taken along the line II-II of FIG. 1 and FIG. 3 showing a top plan view of the diaper 20 of FIG. 1 in its flat-out configuration as well, the diaper 20 has an inner surface 26 facing the wearer, an opposite outer surface 28, a longitudinal centerline L, and a lateral centerline T. The diaper 20 also has longitudinal side edges 22 run generally in the longitudinal direction of the diaper and lateral end edges 24 run between the longitudinal side edges 22 generally in the lateral direction of the diaper 20. The periphery of the diaper 20 is defined by the longitudinal side edges 22 and the lateral end edges 24. The diaper 20 further has a front waist region 36, a back waist region 38 and a crotch region 40 disposed between the front waist region 36 and the back waist region 38.

Figure 5:
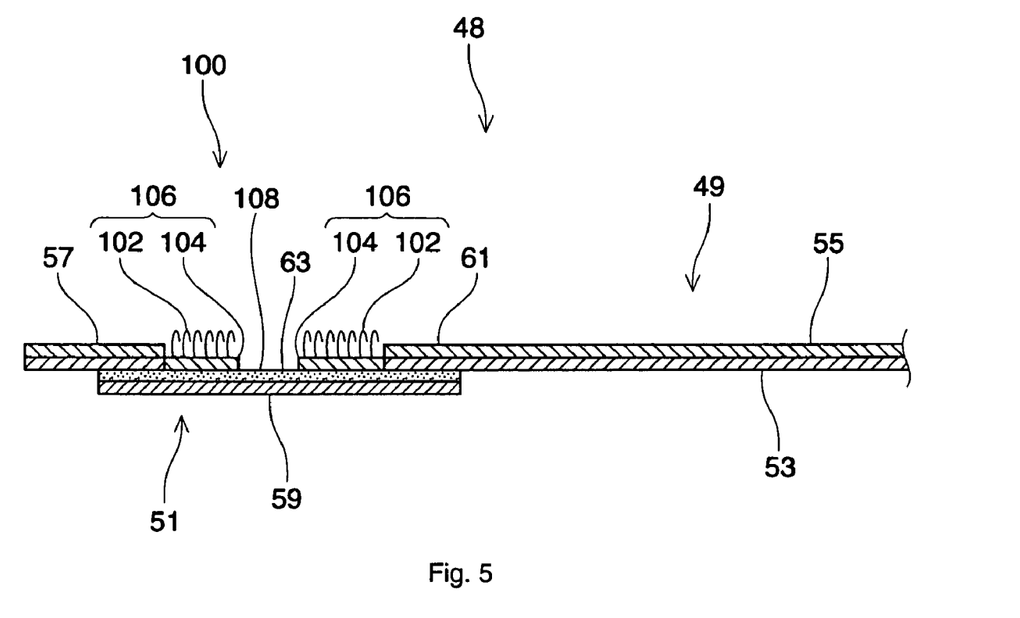
FIG. 5 is a cross-sectional view taken along the line V-V of FIG. 4.

The diaper 20 comprises a chassis 54 and a fastening member 48 joined to the chassis 54. The chassis 54 has a generally rectangle shape in its flat-out configuration as shown in FIG. 3. The chassis 54 has lateral end edges 58 and longitudinal side edges 56. The lateral end edge 58 of the chassis 54 preferably defines the lateral end edge 24 of the diaper 20. The longitudinal side edges 56 of the chassis 54 preferably defines the longitudinal side edge 22 of the diaper 20 at least in the crotch region 40. The chassis 54 comprises a liquid pervious topsheet 30; a liquid impervious backsheet 32; an absorbent core 34, which is preferably positioned between at least a portion of the topsheet 30 and the backsheet 32; and a side flap 44 extending laterally outwardly from the absorbent core 34. The side flap 44 has a proximal flap 74 and a distal flap 76. The chassis 54 further comprises an elasticized outer leg cuff 42 disposed adjacent to the longitudinal side edge 22 in the crotch region 40. The elasticized outer leg cuff 42 has a base 68 and a gasket cuff 70 supported by the base 68 at a joint 72 of the base 68 to the gasket cuff 70. The gasket cuff 70 is provided with an elastic material 46 and has an inner cuff 81 extending laterally inwardly from the joint 72 and an outer cuff 83 extending laterally outwardly from the joint 72. The chassis 54 shown in FIG. 1 also may comprise barrier leg cuffs 52 and an elastic waist feature (not shown in Figures). The fastening member 48 is joined adjacent to the longitudinal side edge 56 of the chassis 54 and joined to an element constituting the chassis 54 such as a topsheet, a backsheet, an absorbent core, an elasticized outer leg cuff, a barrier leg cuff or combinations thereof by any known means such as adhesives or heat and pressure attachment such that the fastening member 48 extends laterally outwardly from the absorbent core 34. In the embodiment shown in FIG. 1, the fastening member 48 is joined to the backsheet 32 by heat and pressure attachment. The fastening member 48 comprises an ear panel or base panel 49 and a tab 51 extending laterally outwardly from the ear panel 49 in stretched configuration of the tab 51 (FIGS. 1 and 3 show the tab 51 being folded laterally inwardly). The fastening member 48 also has fastening materials 100. A landing zone member 94 is provided in the front waist region 36 to form a closure of the diaper 20 together with the fastening materials 100 of the fastening member 48.

The liquid pervious topsheet 30 is preferably positioned adjacent the body-facing surface of the absorbent core 34 and may be joined thereto and/or to the backsheet 32 by any attachment means known in the art. The topsheet 30 is preferably compliant, soft feeling, and non-irritating to the wearer's skin. Further, at least a portion of the topsheet 30 is liquid pervious, permitting liquid to readily penetrate through its thickness. A suitable topsheet 30 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 30 is made of a hydrophobic material or is treated to be hydrophobic in order to isolate the wearer's skin from liquids contained in the absorbent core 34. If the topsheet 30 is made of a hydrophobic material, preferably at least the upper surface of the topsheet 30 is treated to be hydrophilic so that liquids will transfer through the topsheet more rapidly.

The liquid impervious backsheet 32 is generally that portion of the diaper 20 positioned adjacent the garment-facing surface of the absorbent core 34. Backsheet 32 prevents the exudates absorbed and contained therein from soiling articles that may contact the diaper 20, such as bedsheets and undergarments. In preferred embodiments, the backsheet 32 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 32. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. The backsheet 32 may be covered by a woven or a nonwoven to impart more cloth-like appearance to the diaper.

The absorbent core 34 may comprise any absorbent material that is generally compressible, conformable, non-irritating to the wearer's skin, and capable of absorbing and retaining liquids such as urine and other certain body exudates. The absorbent core 34 has longitudinal side edges and end edges and can be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In any case all or a portion of the core may include slits which allow the core to form openings when stretched into which fecal mater can flow. The configuration and construction of the absorbent core 34 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 34 should be compatible with the design loading and the intended use of the diaper 20.

The barrier leg cuff 52 is joined adjacent the longitudinal side edges 56 of the chassis 54. In the embodiment shown in FIG. 2, the barrier leg cuff 52 is joined onto the topsheet 30 at the proximal edge 66 of the barrier leg cuff 52 by any known means. The barrier leg cuff 52 may comprise any known materials such as a nonwoven material which may be liquid impervious and/or hydrophobic. The barrier leg cuff 52 has a lateral inner portion 62 extending laterally inwardly from the proximal edge 66 and being provided with an elastic materials at the distal end of the lateral inner portion 62 to space the lateral inner portion 62 upwardly away from the topsheet 30 to serve as a barrier to leakage of body exudates.

The side flap 44 shown in FIGS. 1, 2 and 3 is disposed adjacent the longitudinal side edge 56 of the chassis 54 so as to extend laterally outwardly from the absorbent core 34 in the embodiment shown in FIG. 2. The side flap 44 is preferably formed with a material which is liquid impervious and/or hydrophobic. The side flap 44 has a proximal flap 74 which is laterally proximate to the absorbent core 34 and a distal flap 76 which extends laterally outwardly from the proximal flap 74. The proximal flap 74 and the distal flap 76 may be formed with an integral material or alternatively may be formed with separate materials joined to each other. The side flap 44 may be formed by a single layer of material, or two or more layers of material.

The elasticized outer leg cuff 42 shown in FIGS. 1, 2 and 3 comprises the side flap 44 and the elastic material 46. The outer leg cuff 42 is a generally T-shaped cuff having a base 68 and a gasket cuff 70 supported by the base 68 at a joint 72 of the base to the gasket cuff 70. The term "generally T-shaped" means that the base branches from the gasket cuff at the joint between the inner cuff and the outer cuff of the gasket cuff such that the base forms an angle with the inner cuff and an angle with an outer cuff in a cross-sectional view when the diaper is in a relaxed configuration. Therefore, the base may form an angle of 90 degree or an angle other than 90 degree with the inner cuff and the outer cuff. The base 68 comprises the proximal flap 74 and extends between the longitudinal side edge of the absorbent core 34 and the joint 72. The gasket cuff 70 comprises the distal flap 76 and disposed on the top of the base 68. The gasket cuff 70 has an inner cuff 81 extending laterally inwardly from the joint 72 and an outer cuff 83 extending laterally outwardly from the joint 72 as shown in FIG. 2. The top gasket cuff surface 86 has a generally flat surface in cross-section as shown in FIG. 2 while it may have a degree of undulation in the longitudinal direction formed by the gather caused by the elastic material 46 as shown in FIG. 1. The gasket cuff 70 is provided with the elastic material 46 such as a plurality of elastic strands, a single elastic belt or the like.

The fastening member 48 extends in the longitudinal direction and in the lateral direction which are corresponds to the longitudinal direction and the lateral direction of the diaper 20. The fastening member 48 comprises an ear panel or base panel 49 and a tab 51 extending laterally outwardly from the ear panel 49 in stretched configuration of the tab 51. The ear panel 49 and the tab 51 may be formed with an integral material or may be formed with separate materials joined to one another. In the embodiment shown in FIGS. 4 and 5, a portion of the tab 51 is integrally formed with the ear panel 49. The fastening member 48 also has fastening materials 100 to form a closure of the diaper 20 with the landing zone member 94.

The ear panel 49 may comprise any material such as a plastic film, woven or nonwoven webs of natural fibers (e.g., wood or cotton fibers), synthetic fibers (e.g., polyester or polypropylene fibers), or a combination of natural and synthetic fibers or may comprise any combination of materials thereof. The ear panel 49 is preferably compliant, soft feeling, and non-irritating to the wearer's skin as the ear panel 49 touches the wearer's skin when in use. Further, at least a portion of the ear panel 49 may be vapor pervious, permitting vapor to readily penetrate through its thickness. In the embodiment shown in FIG. 5, the ear panel 49 comprises a plastic film 53 and a nonwoven 55 laminated on the plastic film 53 such that the nonwoven 55 faces the wearer's body and the plastic film 53 faces outwardly when the diaper 20 is used. The ear panel 49 may have stretchability so that the ear panel 49 is able to provide a force to maintain the diaper on the wearer's body.

The tab 51 may comprise an extension of the ear panel 49 or may comprise separate materials joined to the ear panel 49. The tab 51 may have any shape. The shaped tab 51 shown in FIGS. 4 and 5 comprises a leading portion 57, a connective portion 59, and a trailing portion 61. The trailing portion 61 comprises an extension of the ear panel 49. The leading portion 57 may comprise the same material as the ear panel 49 and/or the connective portion 59 or may comprise different materials. The leading portion 57 serves as a grasp portion for the shaped tab 51. The connective portion 59 preferably comprises a material different from the material of the ear panel 49. This allows to provide the connective portion 59 with properties different from the material of the ear panel 49 with respect to, e.g., stiffness and stretchability. The connective portion 59 may comprise a plastic film, a woven, a nonwoven or a combination thereof. Preferably, the connective portion 59 is stiffer than the ear panel 49. Preferably, the connective portion 59 is less stretchable than the ear panel 49. The connective portion 59 which is stiffer and/or less stretchable than the ear panel 49 reduces the forces developed in the ear panel 49 to be transmitted therethrough. It also reduces the wrinkles created in the ear panel 49 due to the forces developed in the ear panel 49 to be transmitted through the connective portion 59. The connective portion 49 is provided with an adhesive means 63 to join portions of the connective portion 49 to the trailing portion 61 and the leading portion 57.

The fastening material 100 is provided on the shaped tab 51. The fastening material 100 is intended to provide a fastening means for engaging the landing zone member 94 so as to provide a secure side closure for the diaper 20. Thus, the fastening material 100 comprises a first fastening material 106. The first fastening material 106 comprises a first hook fastening material comprising a plurality of hooks 102 and the base substrate 104 to support the hooks 102. The base substrate 104 is joined to the connective portion 59 of the shaped tab 51 through the adhesive means 63. It is preferable that the hooks 102 protrude beyond the surface of the ear panel 49 such that the hooks 102 sufficiently engage into the landing zone member 94. It should be understood that the use of the term "hook" should be non-limiting in the sense that the engaging elements may comprise any shapes as are known in the art so long as they are adapted to engage a complementary landing zone member. The first hook fastening material 106 may comprise any of the well known configurations and securement means for achieving a side closure on a diaper. It is preferable that the first hook fastening material 106 comprises two first hook fastening materials, a proximal first hook fastening material and a distal first hook fastening material, which are spacedly positioned in the lateral direction of the shaped tab 51. The proximal first hook fastening material is positioned adjacent the leading portion 57 and the distal first hook fastening material is positioned adjacent the trailing portion 61. Each of the first hook fastening materials 106 generally extends in the longitudinal direction of the shaped tab 51 and a gap is provided between each of the first hook fastening materials 106. Without wishing to be bound by the theory, it is believed that the gap between the first hook fastening materials 106 contributes to reduce the transmission of the induced stress developed in the proximal first hook fastening material to the distal first hook fastening material to prevent the distal first hook fastening material from being detached from the landing zone member 94. In the embodiment shown in FIGS. 4 and 5, the gap comprises a portion of the connective portion 59 which is stiffer and/or less stretchable than the ear panel 49. This also contributes to reduce not only the transmission of the forces developed and/or wrinkles created in the ear panel 49 through the gap but also the transmission of the induced stress developed in the proximal first hook fastening material to the distal first hook fastening material to prevent the distal first hook fastening material from being detached from the landing zone member 94. The gap may have a lateral width of between about 3 mm and about 15 mm, preferably between about 5 mm and about 13 mm, more preferably between about 7 mm and about 11 mm. While the first fastening material 106 comprises a hook fastening material, the first fastening material 106 may comprise an adhesive material which are spacedly positioned in the lateral direction.

The fastening material 100 may also have a second fastening material 108. The second fastening material 108 comprises a second adhesive material provided at the gap between the first hook fastening material 106. The second adhesive material 108 may comprise the adhesive means 63 of the connective portion 59 or may comprise a different adhesive means. The second adhesive material 108 provides a supplemental fastening means. The second adhesive material 108 may also serve as a means to temporarily attach the shaped tab 51 to the ear panel 49 as shown in FIG. 1 before use of the diaper 20. Alternatively, the second adhesive material 108 may serve as a means to roll up and secure the soiled diaper to dispose it by being joined to the backsheet 32. Such an adhesive material 108 is particularly useful when the outer surface of backsheet 32 comprises a plastic film as the hook means does not engage the plastic film. Alternatively, the second fastening material 108 may comprise a hook fastening material if so desired, especially when the first fastening material 106 comprises an adhesive material. In such a case, it is preferable that a nonwoven outer cover is provided on the outer surface of the backsheet 32 such that the second hook fastening material 108 is engageable to the nonwoven outer cover for disposal of the soiled diaper.

Figure 4:
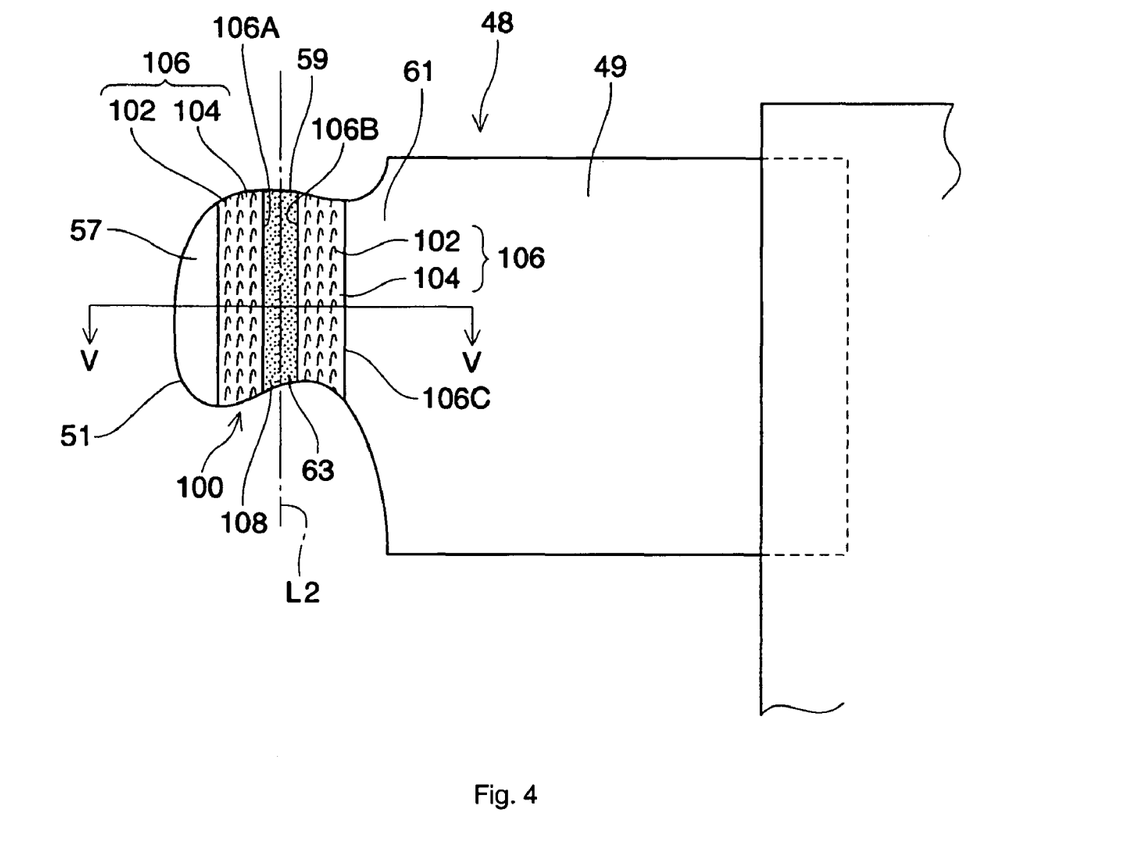
FIG. 4 is an enlarged top plan view of the fastening member.

The fastening member 48 may be folded such that the shaped tab 51 having the fastening material 100 is superposed on the ear panel 49 and engages the nonwoven 55 of the ear panel 49 as shown in FIG. 1. In this configuration, the shaped tab 51 may be folded along the partition line 110 described hereinbelow. Alternatively, the fastening member 48 may be folded at any point of the shaped tab 51 or the ear panel 49. For example, the fastening member 48 may be folded along the line 106A, 106B or 106C as indicated in FIG. 4. When the fastening member 48 is folded along the line 106A or 106B, the second adhesive material 108 is superposed on either of the first hook fastening materials 106. This allows to prevent the adhesion of the second adhesive material 108 from being deteriorated because the second adhesive material 108 only touches the head of the hooks 102.

Figure 6:
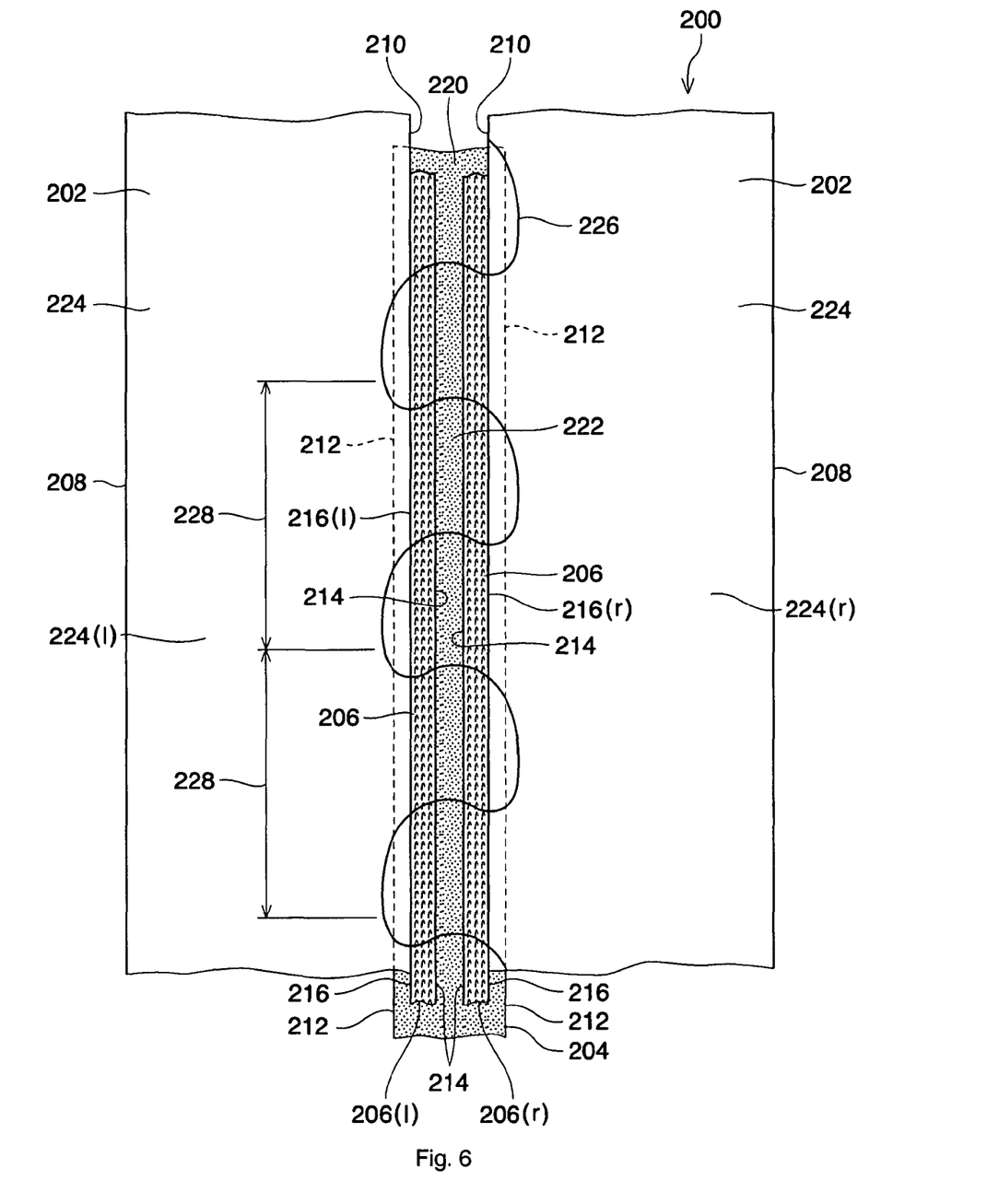
FIG. 6 is a schematic top plan view of a first process forming a plurality of pairs of fastening members.
Figure 7:
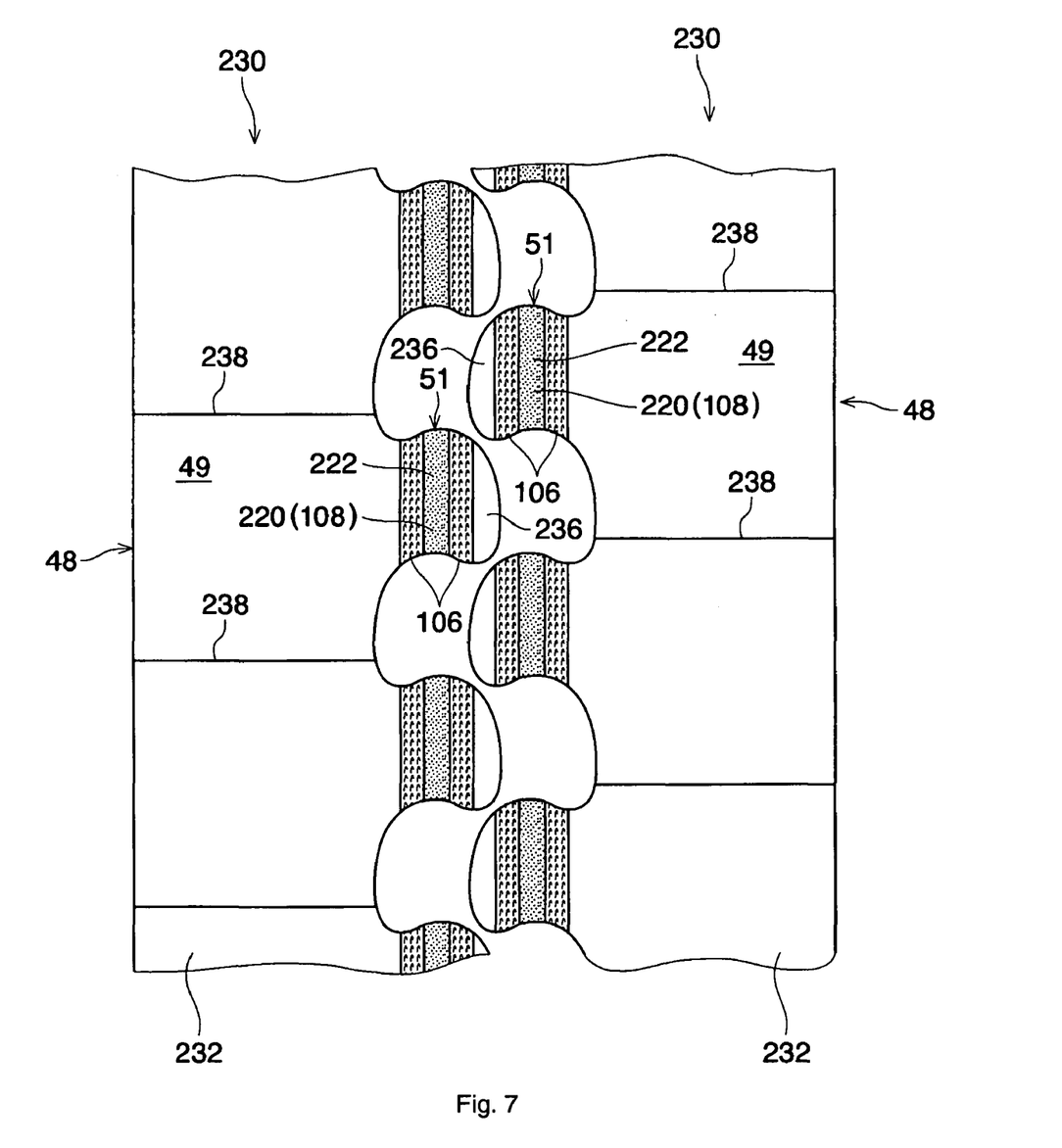
FIG. 7 is a schematic top plan view of a second process forming a plurality of pairs of fastening members.

FIGS. 6 and 7 show a schematic view of a method forming a plurality of pairs of fastening members. The method comprises the step of preparing the continuous fastening composite web extending along a longitudinal direction, the step of cutting the continuous fastening composite web along a continuous cut line to form a pair of continuous fastening members, and the step of cutting each of the continuous fastening members to form a plurality of pairs of fastening members.

In the preparing step, the continuous fastening composite web 200 is prepared. The continuous fastening composite web 200 comprises two longitudinally extending first substrates 202 which are laterally spacedly positioned; a longitudinally extending second substrate 204 positioned between the two first substrates 202; and at least two longitudinally extending first fastening materials 206 laterally spacedly positioned. Each of the first substrate 202 has a longitudinal outer side edge 208 and a longitudinal inner side edge 210. The second substrate 204 has a pair of longitudinal side edges 212. Each of the longitudinally extending first fastening material 206 has a longitudinal inner side edge 214 and a longitudinal outer side edge 216. The first substrate 202 constitutes the ear panel 49 of the fastening member 48. The second substrate 204 constitutes the connective portion 59 of the shaped tab 51. As the first substrate 202 and the second substrate 204 are formed from separate materials, the first substrate 202 and the second substrate 204 can have different properties from one another with respect to, e.g., stiffness and stretchability. This allows to differentiate the properties of a portion of the tab 51 such as the connective portion 59 from the properties of a portion of the ear panel 49. It is preferable that the second substrate 204 is stiffer than the first substrate 202. It is preferable that the second substrate 204 is less stretchable than the first substrate 202. The longitudinally extending first fastening material 206 constitutes the first fastening material 106 such as hook fastening material and adhesive fastening material. In the embodiment shown in FIGS. 6 and 7, the longitudinally extending first fastening material 106 comprises a longitudinally extending first hook fastening material.

A pair of longitudinally extending first substrates 202 are provided such that a gap is provided between the longitudinal inner side edges 210 of the first substrates 202. The pair of first substrates 202 may be provided from two different feeding rolls of the first substrate which are preliminary spaced. Alternatively, the pair of first substrates 202 may be provided by slitting one longitudinally extending first substrate web (not shown in Figures) into the two longitudinally extending first substrates and laterally spacing the two longitudinally extending first substrates.

The longitudinally extending second substrate 204 is provided to the gap between each of the first substrate 202 such that the second substrate 204 forms the connective portion 59 of the shaped tab 51 and overlaps a portion of each of the first substrates 202. The second substrate 204 is then joined to each of first substrates 202. More concretely, each of the longitudinal side edges 212 of the second substrate 204 is joined adjacent to each of the longitudinal inner side edges 210 of the first substrates 202. The second substrate 204 may be joined to the first substrates 202 by any known means such as adhesives or heat and pressure attachment. In the embodiment shown in FIG. 6, an adhesive 220 is provided on the surface of the second substrate 204 and is used for joining the second substrate 204 to the first substrate 202. The adhesive 220 corresponds to the adhesive means 63 of the connective portion 49 shown in FIGS. 4 and 5.

A pair of longitudinally extending first fastening materials 206 may be provided on at least one of the first substrate 202 and the second substrate 204. In the embodiment shown in FIG. 6, the first fastening material 206 is provided on the second substrate 204 and between the first substrate 202 such that the longitudinal outer side edges 216 of the first fastening materials 206 are contiguous with the longitudinal inner side edges 210 of the first substrates 202. Positioning the first fastening material 206 defines a gap region 222 and a panel region 224. The gap region 222 is provided between each of the longitudinal inner side edges 214 of the first fastening materials 206. The gap region 222 substantially comprises the second substrate 204 in FIG. 6. A pair of panel regions 224 are also provided between each of the longitudinal outer side edges 216 of the first fastening material 206 and each of the longitudinal outer side edges 208 of the first substrates 202. Therefore, the panel region 224 substantially comprises the first substrate 202 in FIG. 6. A portion or the entirety of the panel region 224 serves as the ear panel 49. In the embodiment shown in FIG. 6, a portion of the panel region 224 serves as the ear panel 49 and the rest of the panel region 224 serves as the trailing portion 61 of the shaped tab 51 (refer to FIG. 4). The adhesive 220 on the second substrate 204 is exposed through the gap region 222 to serve as the second adhesive material 108 as explained above. The pair of first fastening materials 206 may be provided from two different feeding rolls of the first fastening material which are preliminary spaced. Alternatively, the pair of first fastening materials 206 may be provided by slitting one longitudinally extending first fastening material web (not shown in Figures) into the two longitudinally extending first fastening materials and laterally spacing the two longitudinally extending first fastening materials.

In the preparing step of the continuous fastening composite web hereinabove, a pair of longitudinally extending first substrate are provided such that a gap is provided therebetween, and then the second substrate is provided between the gap and joined to the first substrates. After that, a pair of longitudinally extending first fastening materials are provided on the second substrate 204 and between the first substrate 202. However, the sequence of forming the continuous fastening composite web is variable. For example, the second substrate may be first provided and then a pair of first substrates may be provided to join to the second substrate. After that, a pair of first fastening materials may be provided to join on the second substrate. Alternatively, the second substrate may be first provided and then a pair of first fastening materials may be provided to join on the second substrate. After that, a pair of first substrates may be provided to join to the second substrate. Further alternatively, when the first fastening materials are joined to the first substrate, but not joined to the second substrate, the first fastening material and the first substrate may be first joined. After that, the first substrates may be joined to the second substrate. It should be recognized that many other sequences of forming the continuous fastening composite web are possible within the scope of the present invention.

The continuous fastening composite web 200 thus formed is then cut along a continuous cut line 226. The continuous cut line 226 comprises a plurality of repeating patterns 228. Each one of repeating patterns 228 starts in one panel region (panel region 224 on the left side in the embodiment shown in FIG. 6 (herein, members located on the left side in FIG. 6 are referred to with suffix of "(l)")) laterally outside the longitudinal outer side edge 216(l) of the first fastening material 206(l), extends therefrom through the two first fastening materials 206 and the gap region 222 to reach the other panel region (panel region 224 on the right side in the embodiment shown in FIG. 6 (herein, members located on the right side in FIG. 6 are referred to with suffix of "(r)")) laterally outside the longitudinal outer side edge 216(r) of the first fastening material 206(r), and then extends to return from the other panel region (panel region 224(r)) through the two first fastening materials 206 and the gap region 222 to reach the one panel region (panel region 224(l)).

The continuous fastening composite web 200 cut along the continuous cut line 226 is separated to form a pair of continuous fastening members 230 as shown in FIG. 7. Each of the continuous fastening member 230 has a continuous panel region 232 and a plurality of tabs 51. Each tab 51 has the two first fastening materials 106 spacedly positioned on the tab 51. In the gap region 222 between the two first fastening materials 106, the adhesive 220 is exposed to serve as the second fastening material 108 (e.g., second adhesive material). Each tab 51 also has a grasp portion 236 at a distal portion of the tab 51. The grasp portion 236 is formed as the continuous cut line 226 is designed to extend into each opposite panel region 224 shown in FIG. 6.

Each of continuous fastening members 230 is then cut across the continuous panel region 232 along a lateral cut line 238 to form a plurality of pairs of fastening members 48. Each fastening member 48 comprises the base panel 49 and the tab 51 as described above. In the embodiment shown in FIG. 7, the lateral cut line 238 extends straightly in the lateral direction. However, the lateral cut line may be any shape such as a curved line or a wavy line as far as the lateral cut line separates the continuous fastening member 230 into a plurality of discrete fastening members 48. The pair of fastening members 48 thus formed is then joined to the opposite longitudinal side edges 56 of the chassis 54.

Figure 8:
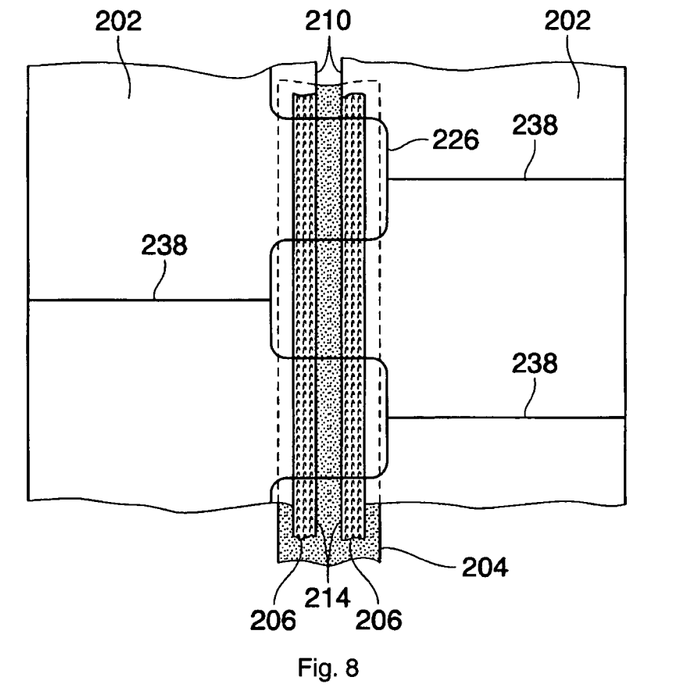
FIG. 8 is a schematic top plan view of a process forming an alternative embodiment of fastening members.

Many alternatives are possible in forming a fastening member of the present invention while only representative examples are described herein below. FIG. 8 shows an alternative embodiment of forming a plurality of pairs of fastening members. In the embodiment shown in FIG. 8, the shape of the continuous cut line 226 is different from that of the continuous cut line 226 shown in FIG. 6. The lateral cut line 238 extends straightly in the lateral direction. The longitudinally extending first fastening materials 206 are joined to the longitudinally extending first substrates 202 without being joined to the second substrate 204. In the embodiment shown in FIG. 8, each of the longitudinal inner side edges 214 of the first fastening materials 206 aligns to each of the longitudinal inner side edges 210 of the first substrates 202. Alternatively, the first fastening material 206 may be disposed on the first substrate 202 such that the longitudinal inner side edge 214 of the first fastening material 206 is spaced from the longitudinal inner side edge 210 of the first substrate 202. The first fastening material 206 may be joined to the first substrate before or after the first substrate 202 is joined to the second substrate 204.

Figure 9:
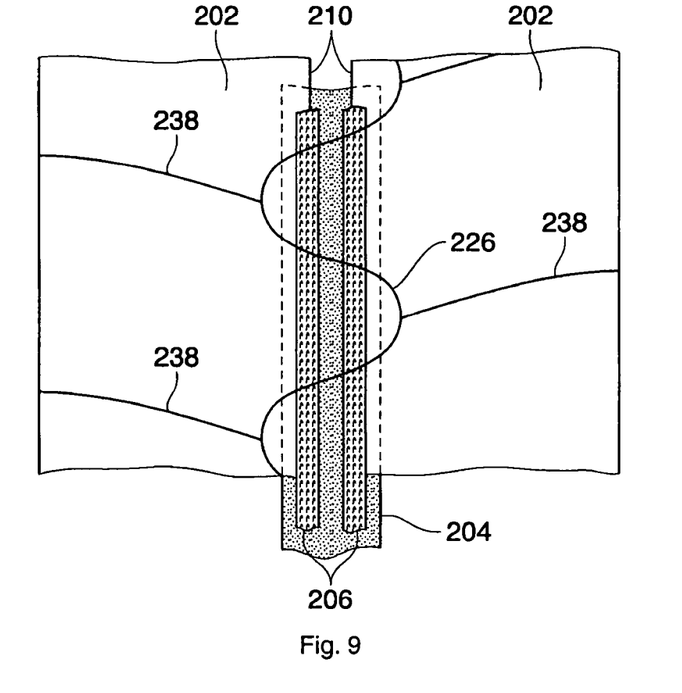
FIG. 9 is a schematic top plan view of a process forming a further alternative embodiment of fastening members.

FIG. 9 shows a further alternative embodiment of forming a plurality of pairs of fastening members. In the embodiment shown in FIG. 9, the shape of the continuous cut line 226 is different from those of the continuous cut line 226 shown in FIGS. 6 and 8. The shape of the lateral cut line 238 is also different from those of the lateral cut line 238 shown in FIGS. 6 and 8. More concretely, the lateral cut line 238 shown in FIG. 9 is curved, instead of being straight. The longitudinally extending first fastening materials 206 are joined to both the longitudinally extending first substrates 202 and the second substrate 204. The longitudinal inner side edge 210 of the first substrate is positioned underneath the first fastening material 206. The first fastening material 206 may be joined to the first substrate before or after the first substrate 202 is joined to the second substrate 204.

Figure 10:
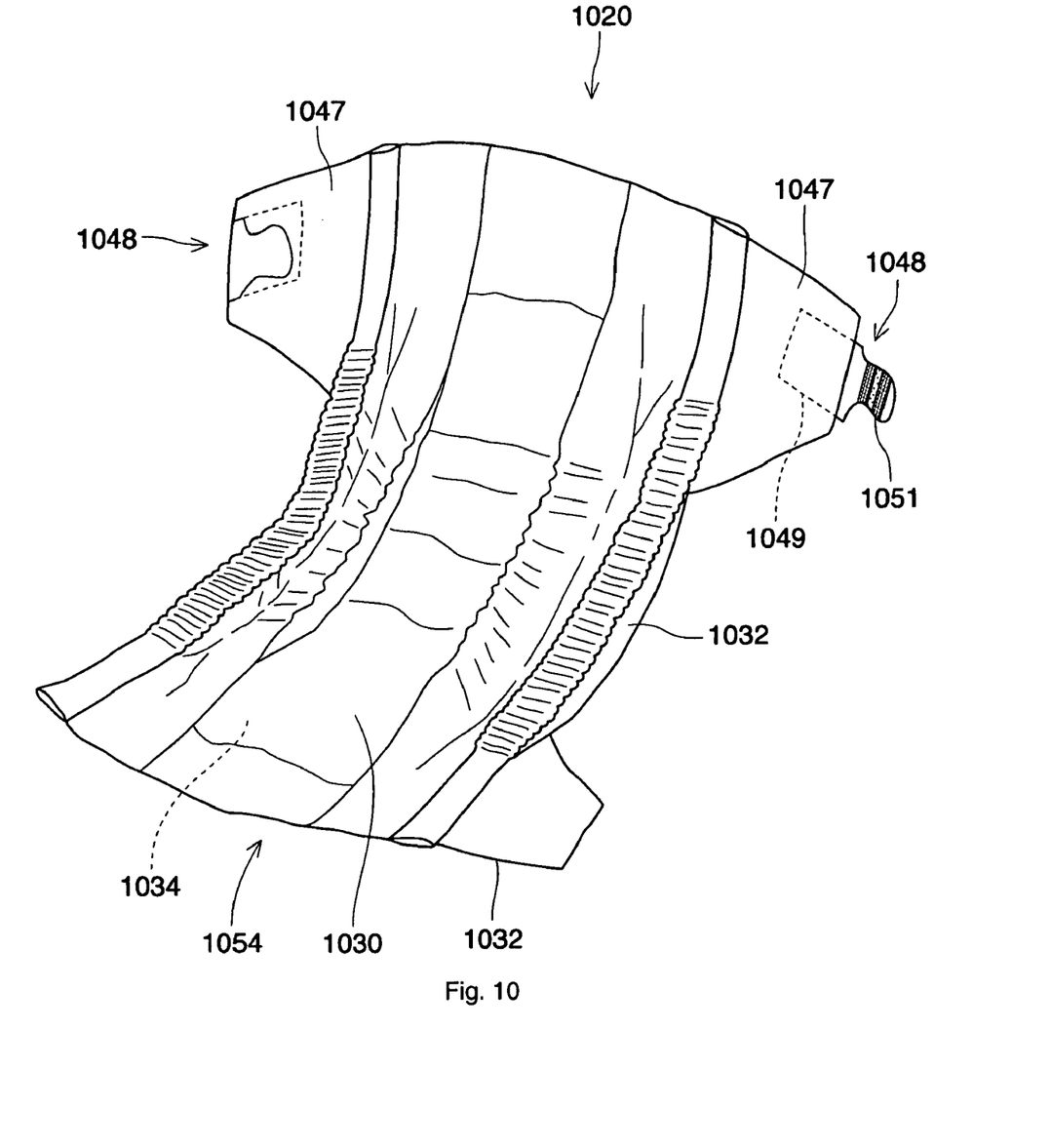
FIG. 10 is a perspective view of an alternative embodiment of a diaper having an alternative fastening member.

FIG. 10 shows an alternative embodiment of a diaper having a fastening member. The diaper 1020 comprises a chassis 1054 and a side panel 1047 joined to the chassis 1054. The chassis 1054 has a liquid permeable topsheet 1030, a liquid impermeable backsheet 1032, and an absorbent core 1034. In the embodiment shown in FIG. 10, the side panel 1047 is formed with an integral extension of the backsheet 1032 (e.g., an extension of a liquid impermeable film or an extension of an outer nonwoven covering the liquid impermeable film). Therefore, the backsheet 1032 of the diaper 1020 has a generally hourglass shape having a narrow crotch region. The diaper 1020 is also provided with the fastening member 1048. The fastening member 1048 is provided in the form of a fastening tape and comprises a shaped tab 1051 and a base panel 1049. The most portion of the base panel 1049 is used to join the fastening member 1048 to the side panel 1047.

While particular embodiments of the present invention have been illustrated and described, it would be apparent to those skilled in the art that various other changes and modifications can be made without departing from the spirit and scope of the present invention. It is therefore intended to cover in the appended claims all such changes and modifications that are within the scope of this invention.

What is claimed is:

1. A method for forming a plurality of pairs of fastening members, each fastening member extending in a longitudinal direction and in a lateral direction and comprising a base panel and a tab extending laterally from the base panel, the tab having first fastening materials laterally spacedly positioned, wherein the method comprising the steps of:

(a) preparing a continuous fastening composite web extending along a longitudinal direction; the continuous fastening composite web comprising two longitudinally extending first substrates laterally spacedly positioned, a longitudinally extending second substrate positioned between the two first substrates, and at least two longitudinally extending first fastening materials laterally spacedly positioned; each of the first substrate having a longitudinal outer side edge and a longitudinal inner side edge; the second substrate having a pair of longitudinal side edges; each of the first fastening material having a longitudinal inner side edge and a longitudinal outer side edge; wherein each of the longitudinal side edges of the second substrate is joined adjacent each of the longitudinal inner side edges of the first substrates, and each of the first fastening materials is joined to the second substrate such that the longitudinal outer side edges of each first fastening material are contiguous with the longitudinal inner side edges of the first substrates and to define a gap region between each of the longitudinal inner side edges of the first fastening materials and to define a pair of continuous panel regions between each of the longitudinal outer side edges of the first fastening materials and each of the longitudinal outer side edges of the first substrates, wherein the second substrate is provided with a second fastening material which is exposed at the gap region, wherein the second fastening material is different from the first fastening materials, (b) cutting the continuous fastening composite web along a continuous cut line comprising a plurality of repeating patterns, each of the repeating patterns having a first side and a second side, the first and second sides extending from one panel region through the two first fastening materials to extend into the other panel region and extending to return from the other panel region through the two first fastening materials to extend into the one panel region, thereby forming a pair of continuous fastening members, each continuous fastening member having a continuous panel region and a plurality of tabs, each tab having the two first fastening materials spacedly positioned, and (c) cutting each of the continuous fastening members across the continuous panel region, thereby forming a plurality of pairs of fastening members, each fastening member comprising the base panel and the tab.

2. The method for forming a plurality of pairs of fastening members according to claim 1 wherein the preparing step includes the step of slitting one longitudinally extending first substrate web into the two longitudinally extending first substrates and the step of laterally spacing the two longitudinally extending first substrates.

3. The method for farming a plurality of pairs of fastening members according to claim 1 wherein the preparing step includes the step of slitting one longitudinally extending first fastening material web into the two longitudinally extending first fastening materials and the step of laterally spacing the two longitudinally extending first fastening materials.

4. The method of forming a plurality of pairs of fastening members according to claim 1 wherein the gap region comprises the second substrate.

5. The method of forming a plurality of pairs of fastening members according to claim 1 wherein the panel region comprises the first substrate.

6. The method of forming a plurality of pairs of fastening members according to any claim 1 wherein the second substrate is stiffer than the first substrate.

7. The method for forming a plurality of fastening members according to claim 1 wherein the first fastening material is a mechanical fastening material and the second fastening material is an adhesive.

* * * * *

UNITED STATES PATENT AND TRADEMARK OFFICE
CERTIFICATE OF CORRECTION

PATENT NO. : 7,371,302 B2 Page 1 of 1
APPLICATION NO. : 10/623882
DATED : May 13, 2008
INVENTOR(S) : Kouichi Miyamoto et al.

It is certified that error appears in the above-identified patent and that said Letters Patent is hereby corrected as shown below:

On the Title Page

Under Item (75) Inventors:

Line 1, delete "Kobe Hyogo (JP)" and insert -- Beijing P.C. (CN) --.

Line 2, delete "Fujisawa Kanagawa" and insert -- Yokohama --.

Lines 3-4, delete "Osaka Osaka" and insert -- Yokohama --.

Under Item (57) Abstract:

Line 3, delete "dircetion" and insert -- direction --.

Col. 14 Claim 3

Line 5, delete "farming" and insert -- forming --.

Signed and Sealed this

Eleventh Day of November, 2008

JON W. DUDAS
*Director of the United States Patent and Trademark Office*